(12) United States Patent
Boss et al.

(10) Patent No.: US 7,139,072 B1
(45) Date of Patent: Nov. 21, 2006

(54) HANDHELD THERMO-ELECTRICALLY COOLED SURFACE-ENHANCED RAMAN SPECTROSCOPY (TEC-SERS) FIBER OPTIC PROBE

(75) Inventors: Pamela A. Boss, San Diego, CA (US); Gregory W. Anderson, San Diego, CA (US); Stephen H. Lieberman, La Mesa, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 442 days.

(21) Appl. No.: 10/845,415

(22) Filed: May 11, 2004

Related U.S. Application Data

(63) Continuation-in-part of application No. 10/413,188, filed on Apr. 14, 2003, now Pat. No. 6,947,132.

(51) Int. Cl.
*G01J 3/44* (2006.01)
(52) U.S. Cl. ..................................................... 356/301
(58) Field of Classification Search ................ 356/301, 356/302, 303, 36–38
See application file for complete search history.

(56) References Cited

U.S. PATENT DOCUMENTS 4,886,358 A * 12/1989 Pellenbarg et al. ......... 356/301
6,967,717 B1 * 11/2005 Boss et al. .................. 356/301

* cited by examiner

*Primary Examiner*—Layla G. Lauchman
(74) *Attorney, Agent, or Firm*—Peter A. Lipovsky; Michael A. Kagan; Allan Y. Lee

(57) ABSTRACT

A thermoelectrically cooled surface-enhanced Raman Spectroscopy (TEC-SERS) fiber optic probe for real-time and in-situ monitoring of volatile organic compounds in gas, liquid, and soil environments. The TEC-SERS probe comprises a sample chamber for receiving a gas sample and a fiber optic Raman probe. The sample chamber comprises an inlet having a semipermeable membrane for separating moisture from the gas sample, a SERS substrate mounted on a thermoelectric cooler, a mass flow device for providing airflow, and an output port. The fiber optic Raman probe is operably coupled to a transparent window in the sample chamber for directing an optical excitation signal to irradiate the SERS substrate and for receiving a SERS optical signal from analytes from the gas sample that are in contact with the SERS substrate.

10 Claims, 6 Drawing Sheets

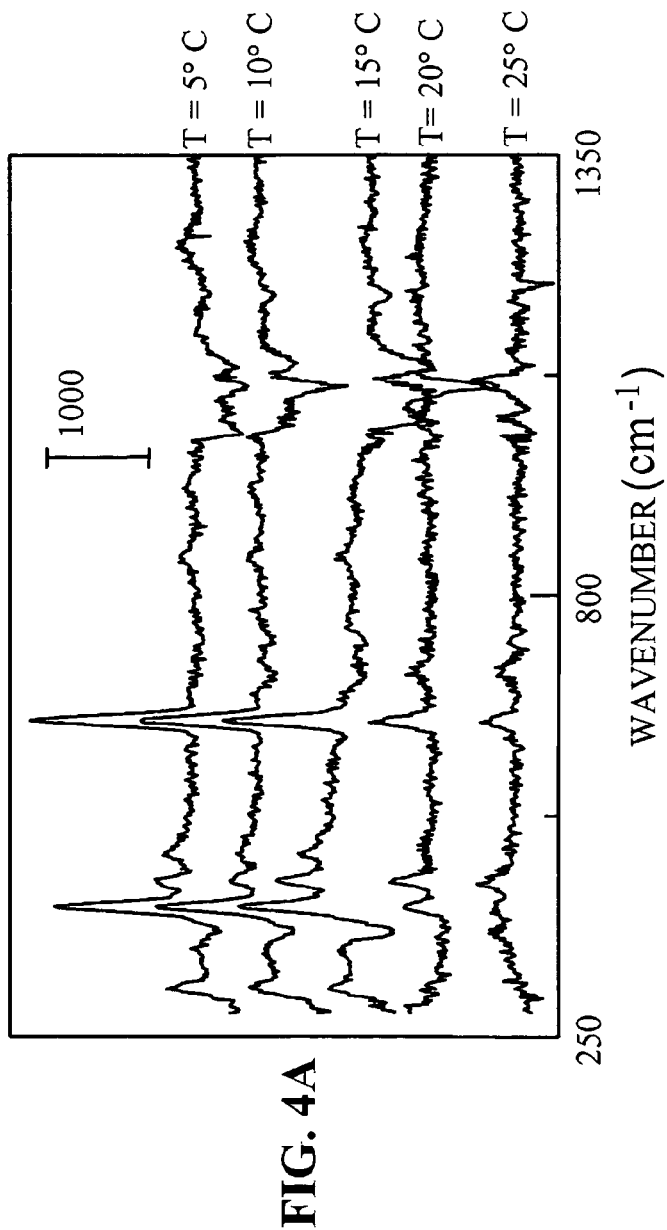
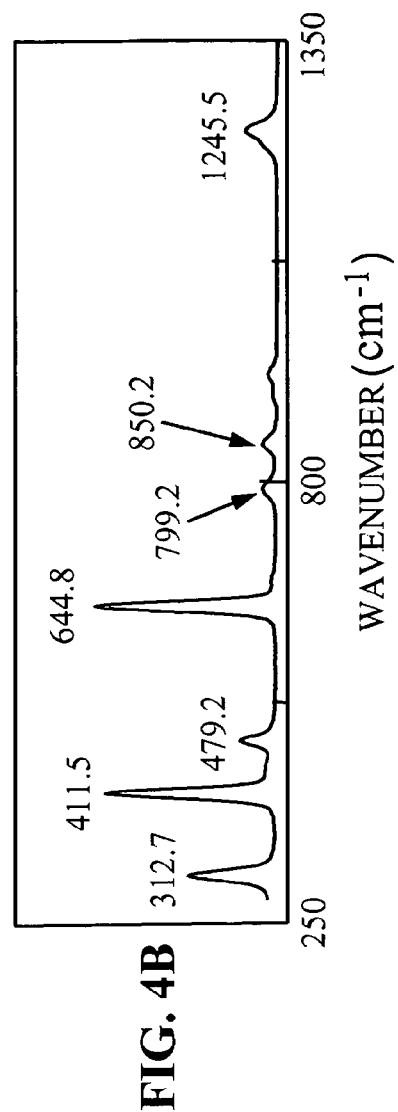
FIG. 4A
FIG. 4B

HANDHELD THERMO-ELECTRICALLY COOLED SURFACE-ENHANCED RAMAN SPECTROSCOPY (TEC-SERS) FIBER OPTIC PROBE

CROSS REFERENCE TO RELATED APPLICATIONS

This application is a continuation-in part of commonly assigned U.S. patent application Ser. No. 10/413,188, entitled THERMO-ELECTRICALLY COOLED SURFACE ENHANCED RAMAN SPECTROSCOPY SENSOR SYSTEM TO DETECT VOLATILE ORGANIC COMPOUNDS, filed 14 Apr. 2003 now U.S. Pat. No. 6,947,132, which is hereby incorporated by reference.

BACKGROUND OF THE INVENTION

The invention relates generally to the field of Raman spectroscopy. More specifically, the invention relates to a handheld fiber optic probe that uses a thermoelectric cooler (TEC) to condense volatile organic compounds (VOCs) onto a SERS substrate for real-time monitoring and in-situ monitoring of VOCs in gas, liquid, and soil environments.

Raman spectroscopy is an emission technique that involves inelastic scattering of incident laser energy and results in spectral peaks that are frequently shifted from the incident energy. The Raman bands arise from changes in polarizability in a molecule during vibration. As a result, virtually all organic molecules display a characteristic Raman emission. Therefore, a Raman-based sensor would not be limited to a specific class of molecules as is the case for the laser induced fluorescence (LIF) sensor. FIG. 1 shows Raman spectra obtained for carbon tetrachloride ($CCl_4$), chloroform ($CHCl_3$), and methylene chloride ($CH_2Cl_2$). These chlorinated solvents vary in the number of hydrogen and chlorine atoms. Yet they can easily be distinguished by their Raman spectra. Unlike fluorescence, the Raman peaks are very narrow. The inherently high resolution of Raman spectra often permits the analysis and identification of several components in a mixture simultaneously.

Despite the advantages of Raman spectroscopy over other spectroscopic techniques, Raman spectroscopy is, inherently, an insensitive technique. In the 1970s, it was discovered that Raman scattering from molecules adsorbed on such noble metals as silver, copper, and gold can be enhanced by as much as $10^6$ to $10^7$. The phenomenon, surface-enhanced Raman spectroscopy (SERS), has been the subject of intensive theoretical and experimental research. More than one mechanism is involved in the SERS phenomenon. Initially, the SERS technique was used as a means to probe adsorption at metal interfaces both in electrochemical and gas-phase environments. This technique has proven useful in deducing the effects of interfacial structure and reactivity on the adsorption process. However, the sensitivity of the technique as well as its exceptional spectral selectivity has made SERS attractive for a broad range of analytical applications. SERS can be used for trace organic analysis and as a detection method in gas chromatography, liquid chromatography, and thin layer chromatography. Electrochemical SERS and SERS of chemically modified surfaces have been used to detect aromatic compounds and chlorinated hydrocarbons, organic contaminants of environmental concern, in the ppm concentration range.

Although SERS is very sensitive, the technique requires intimate contact between the SERS active surface and analyte. In turn, this requires that the analyte adsorbs to the SERS active surface. If SERS spectra need to be obtained in real time and in-situ, then the reaction between the SERS substrate and the analyte needs to be reversible.

A sensor design which would (1) be compact and robust and (2) extract VOC vapors from the air and concentrate them onto the SERS substrate would result in a sensor that could be used to monitor VOCs in real time and in-situ. Besides environmental monitoring, such a sensor could be used for homeland security and force protection. There is a real concern that terrorists could poison water supplies using readily available toxic industrial chemicals such as the BTEX compounds and chlorinated solvents.

BRIEF DESCRIPTION OF THE DRAWINGS

For a more complete understanding of the handheld TEC-SERS fiber optic probe, reference is now made to the following detailed description of the embodiments as illustrated in the accompanying drawings, wherein:

(d) FIG. 4A shows the spectra of Ag/TP-TCE exposed to TCE as a function of temperature. Spectra was obtained using 785 nm excitation at 62.8 mW power and a 60 s acquisition time. The gas flow rate was varied between 9–12 mL/min. The spectral features of the coating have been subtracted out.

(e) FIG. 4B shows the normal Raman spectrum of neat TCE.

DESCRIPTION OF THE EMBODIMENTS

Figure 1:
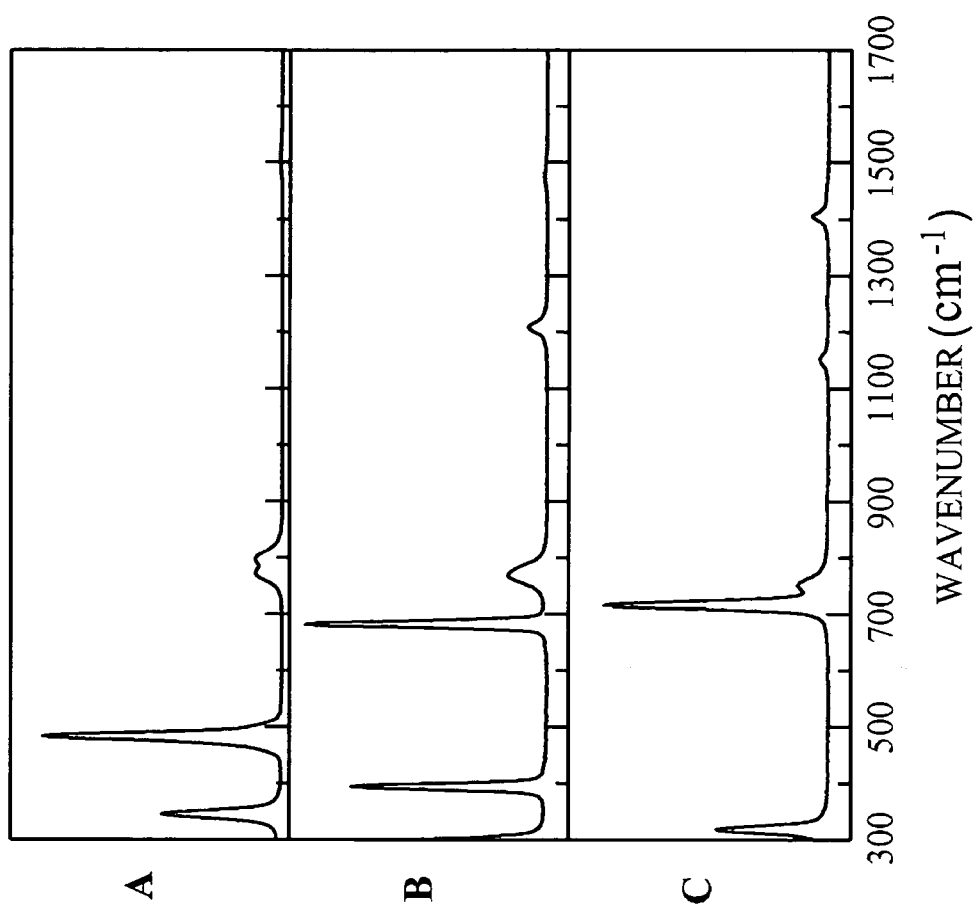
FIG. 1 shows Raman spectra for (A) carbon tetrachloride ($CC1_4$), (B) chloroform ($CHCl_3$), and (C) methylene chloride ($CH_2Cl_2$).
Figure 2:
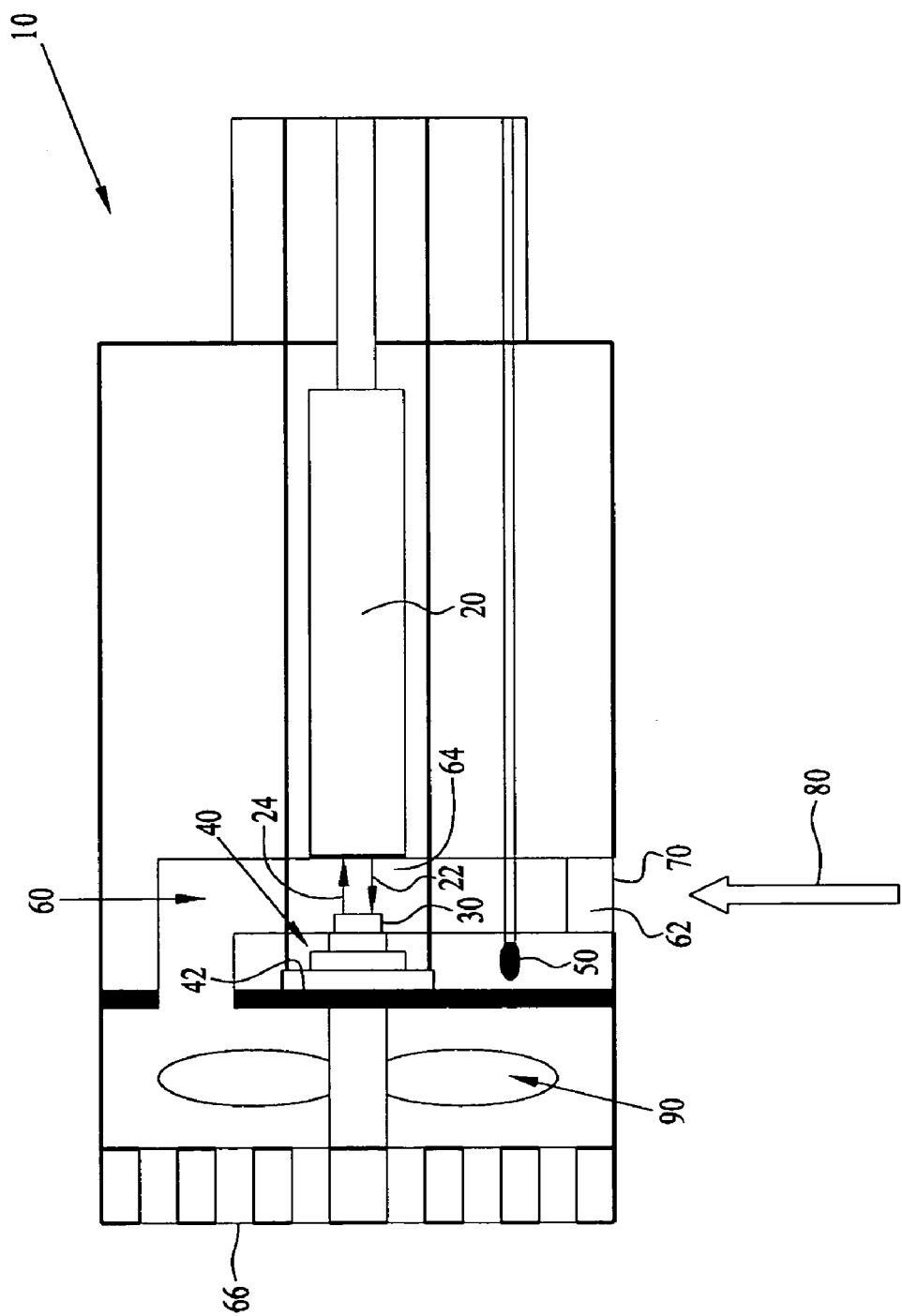
FIG. 2 shows a schematic of the TEC-SERS fiber optic probe.

FIG. 2 shows a schematic of the handheld TEC-SERS fiber optic probe 10. TEC-SERS fiber optic probe 10 comprises commercially available fiber optic Raman probe 20 (see for example, RamanProbe™ from InPhotonics), SERS substrate 30, thermoelectric cooler (TEC) 40, and sample chamber 60. Sample chamber 60 has inlet 62 that comprises semipermeable, such as silicone, membrane 70 to prevent water and particles from entering sample chamber 60. However, silicone membrane 70 will allow analytes 80, which may be gas or vapors, through. Sample chamber 60 comprises SERS substrate 30 that is mounted on miniature thermoelectric cooler (TEC) 40. An example of a TEC that can be used is available from Melcor (part number 3 OT 1.3-46-F9), which has three stages; is 8.8 mm wide and 5.8 mm tall; and is capable of a $\Delta T_{MAX}$ of 109° C. Thermistor 50 is used to monitor the temperature of TEC 40. Because different analytes condense at different temperatures, a controller (not shown) controls the temperature of TEC 40 to facilitate condensation of analytes 80 that may be present in sample chamber 60 onto SERS substrate 30. When in contact with each other, analytes 80 and SERS substrate 30 are stimulated by laser excitation signal 22 to produce Raman emissions signals 24, each emission signal unique to a particular analyte.

Fan 90 is used to bring air into sample chamber 60 via inlet 62 and air out of sample chamber 60 via vent 66. Vent 66 also allows fan 90 to maximize air flow to transfer heat away from the hot side 42 of TEC 40. TEC 40 concentrates analytes 80 onto SERS substrate 30, where they are detected and identified by their characteristic Raman signature. Fiber optic Raman probe 20, which houses the appropriate optical filters to remove Raman emissions due to the optical fibers, delivers the laser excitation signal 22 to SERS substrate 30 through transparent window 64 of sample chamber 60. The irradiation of SERS substrate 30 by laser excitation signal 22 in the presence of analytes 80 causes the generation of SERS emissions signal 24. Fiber optic Raman probe 20 then transports Raman emissions signal 24 to a spectrometer (not shown) for speciation.

Figure 3:
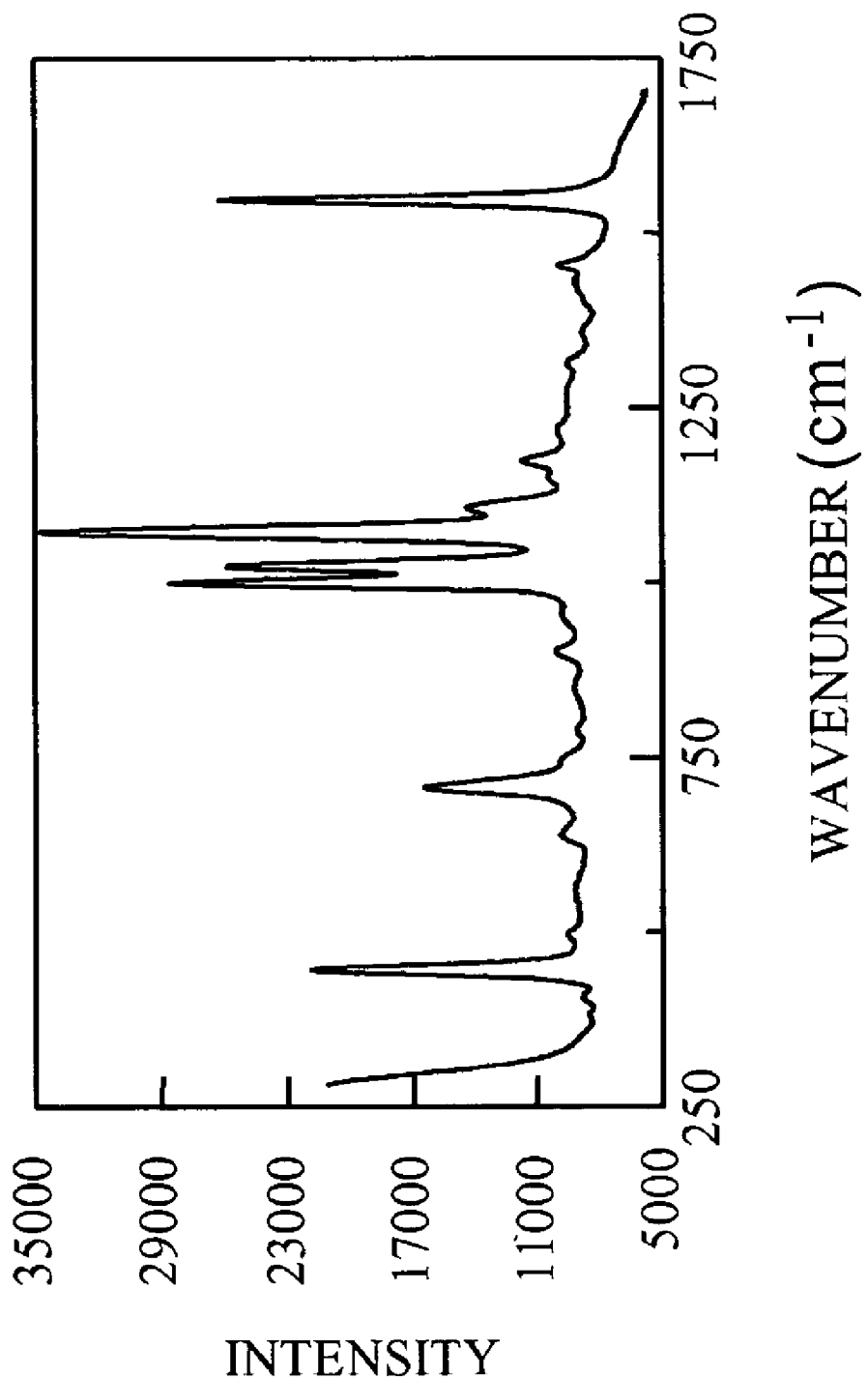
FIG. 3 shows the SERS spectrum of Ag/thiophenol (TP).

SERS substrate 30 of FIG. 2 comprises a silver substrate with a thiophenol (TP) coating. Other coatings besides TP can be used. The coating protects SERS substrate 30 from degradation, thereby extending its lifetime. As shown in FIG. 3, the coating exhibits its own characteristic SERS spectrum that can be used for calibration purposes. If a coating is used that has an affinity for the organic vapor, higher TEC temperatures can be used to concentrate the vapors onto SERS substrate 30. The same SERS substrate was used to generate the data shown in FIGS. 3–5 over a one-month period. Little deterioration in the SERS signal of the coating was observed indicating that the coating protects the SERS surface from degradation and that these substrates can be used for long-term monitoring purposes.

Figure 5A:
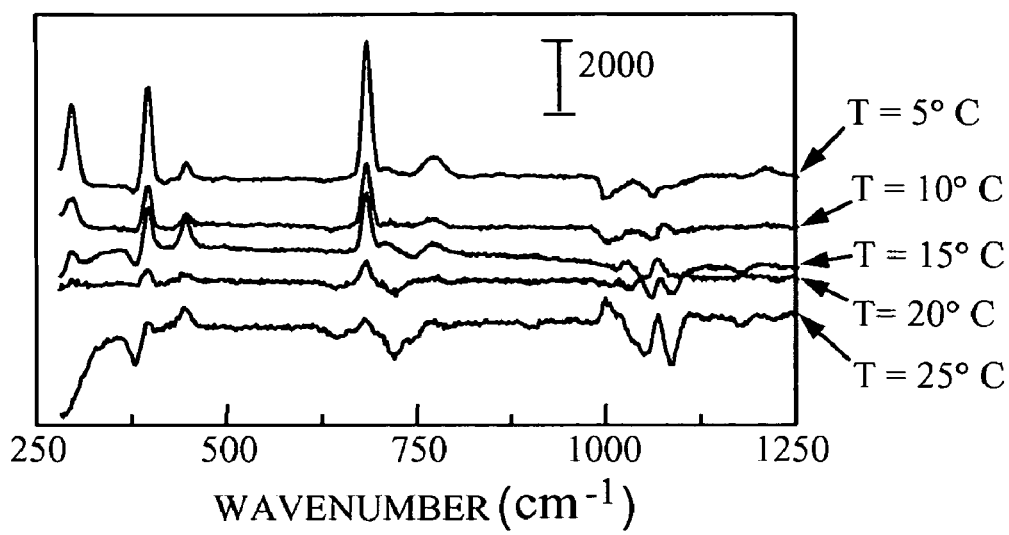
FIG. 5A shows the spectra of Ag/TP-chloroform exposed to chloroform as a function of temperature. The spectral features of the coating have been subtracted out.
Figure 5B:
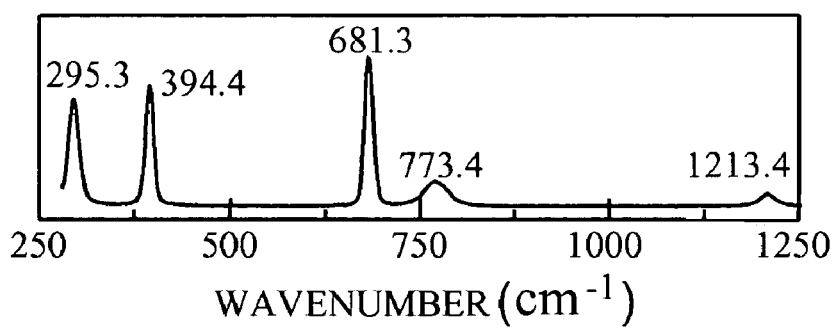
FIG. 5B shows the normal Raman spectrum of neat chloroform.
Figure 5C:
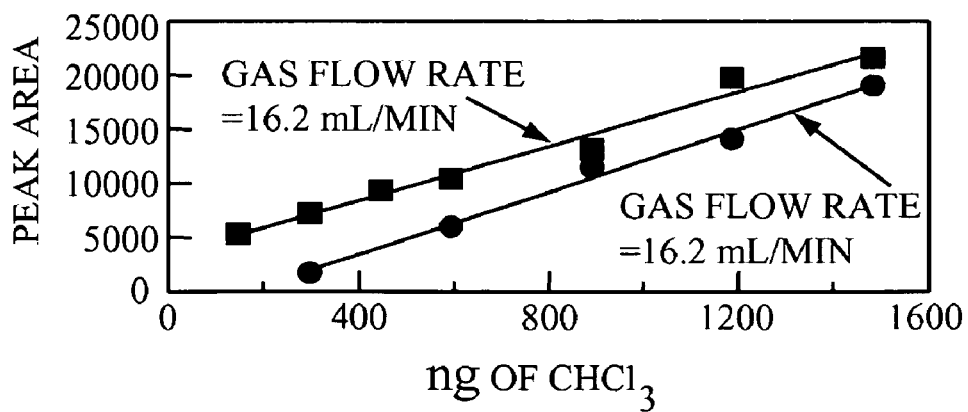
FIG. 5C shows the chloroform concentration response at $T=-10°$ C. and gas flow rates of 16.2 and 5.5 mL/min.

FIGS. 4 and 5 summarize the results obtained for the Ag/TP-TCE and Ag/TP-chloroform systems. As shown in FIGS. 4A and 4B and FIGS. 5A and 5B, the TCE and chloroform peaks in the SERS spectra directly correspond to the peaks observed in the normal Raman spectra of the neat solvent. This facilitates speciation. Volatile organic compounds (VOCs) that have been measured using TEC-SERS include the BTEX (benzene-toluene-ethylbenzene-xylene) compounds, chlorinated solvents, and MTBE (methyl-t butyl ether). The magnitude of the measured VOC response is dependent upon the chemical natures of the coating and the VOC, the temperature of the SERS substrate, and the gas flow rate. The response is reversible. Raising the temperature of the TEC drives off the adsorbed VOCs on the SERS surface. The concentration response of the 681.3 cm$^{-1}$ peak of chloroform at two different gas flow rates is shown in FIG. 5C. The chloroform peak area varies linearly with concentration. The limit of detection (LOD) was determined using the limit calculation method, which states that $$LOD = \frac{3\sigma}{m}$$

where σ is the uncertainty in the y-intercept and m is the slope of the line. For a gas flow rate of 16.2 mL/min, the LOD=158 ng chloroform and for a gas flow of 5.5 mL/min, the LOD is 106 ng. Lowering the gas flow rate results in lower LODs. Besides lowering the gas rate, longer sampling times will also result in lower LODs.

Figure 6:
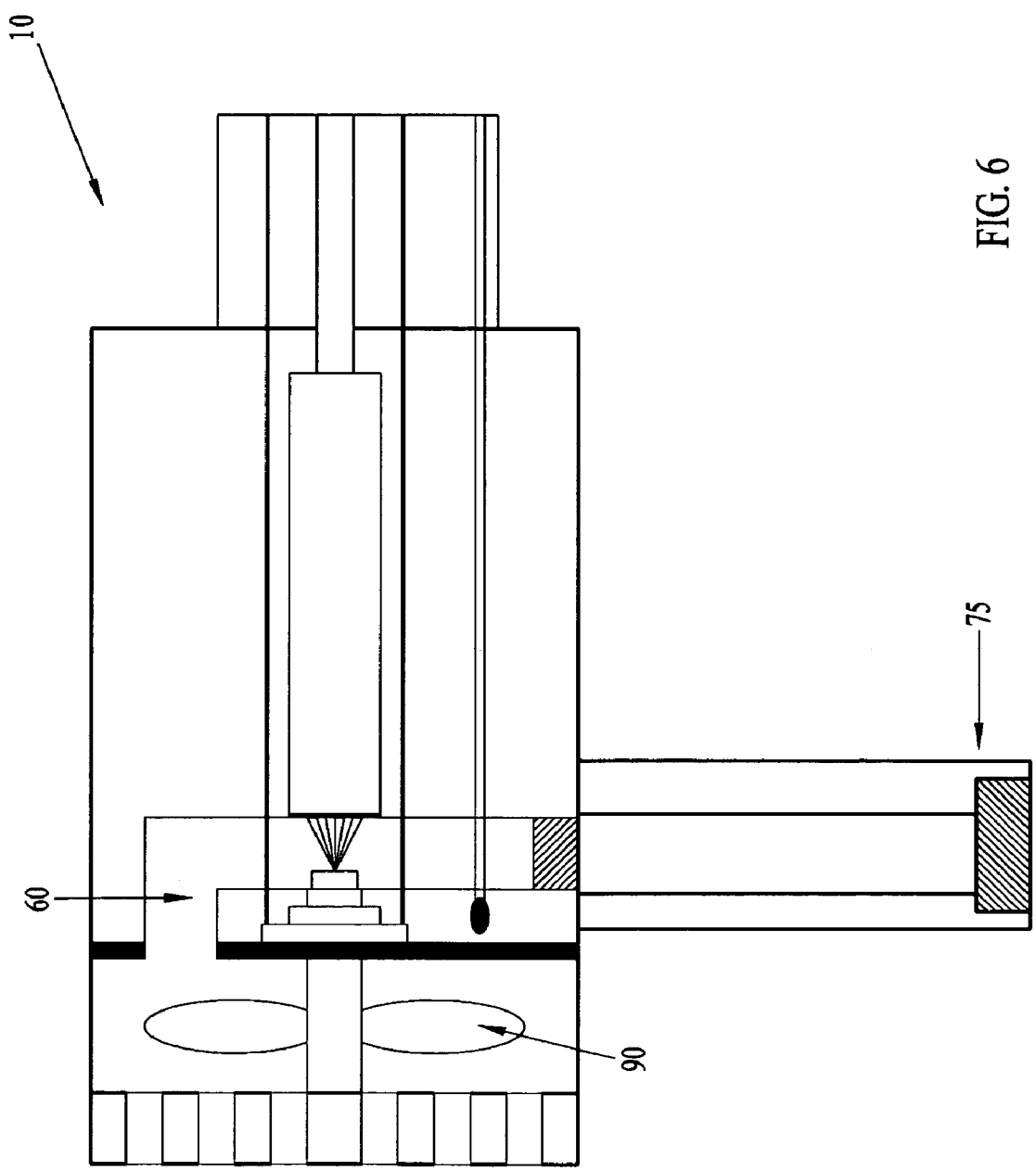
FIG. 6 shows a heated membrane unit attached to the inlet of the TEC-SERS fiber optic Raman probe.

To detect VOCs in aqueous and soil samples, heated membrane unit 75 is attached to inlet 62 of TEC-SERS fiber optic Raman probe 10, as shown in FIG. 6. The Membrane Interface Probe (MIP) from Geoprobe® Systems, Inc. comprises a heated membrane interface that may be used. The MIP comprises a gas permeable membrane brazed onto a steel block that contains a resistive heater coil and a thermocouple, allowing the temperature of the membrane to be controlled and monitored. Heated membrane unit 75 is in contact with the water/soil and is used to volatilize the VOC vapors. Fan 90 of TEC-SERS fiber optic probe 10 transports the VOCs through silicone membrane 70 and into sample chamber 60 for detection and identification as described above.

The handheld TEC-SERS fiber optic probe has many advantages, including: (1) The TEC-SERS probe is compact and robust. (2) A silicone membrane prevents water and particulates from entering the sample chamber. (3) A fan, or other mass flow device, transports vapors into the sample chamber for analysis. (4) The TEC condenses vapors onto the SERS substrate. (5) The constituents of the vapors are identified and quantified by their characteristic Raman response. (6) Adsorption/desorption of VOCs on the SERS substrate is reversible. The coating on the SERS substrate has an affinity for the VOCs. As a result, higher temperatures can be used to condense the VOCs onto the SERS substrate. (7) The coating on the SERS substrate protects the SERS surface from degradation, thereby extending the usable lifetime of the SERS substrate. (8) A heated membrane can be attached to the inlet of the fiber-optic probe to extract VOC vapors from aqueous and solid surfaces. As a result, the device can be used to detect VOCs in either the vapor, aqueous, or solid phases.

Clearly, many modifications and variations of the handheld TEC-SERS fiber optic probe are possible in light of the above teachings. It is therefore to be understood that within the scope of the appended claims the handheld TEC-SERS fiber optic probe may be practiced otherwise than as specifically described.

We claim:

1. A thermo-electrically cooled surface enhanced Raman Spectroscopy (TEC-SERS) fiber optic probe, comprising:
    a sample chamber for receiving a gas sample, said chamber comprising:
        an inlet having a semipermeable membrane for separating moisture from said gas sample;
        a thermoelectric cooler for concentrating said gas sample onto a SERS substrate having top and bottom surfaces, wherein said bottom surface of said substrate is mounted on said thermoelectric cooler and said top surface is opposed to a transparent window in said sample chamber;
        a mass flow device operably coupled to said sample chamber for providing airflow in said sample chamber;
        an output port for transporting said gas sample out of said sample chamber; and
    a fiber optic Raman probe operably coupled to said window in said sample chamber for directing an optical excitation signal to irradiate said SERS substrate and for receiving a SERS optical emissions signal.

2. The TEC-SERS fiber optic probe of claim 1 wherein said SERS substrate comprises a protective layer on said top surface.

3. The TEC-SERS fiber optic probe of claim 2 wherein said protective layer is selected from the group consisting of organic thiols, organosilanes, and polymers.

4. The TEC-SERS fiber optic probe of claim 1 wherein said mass flow device is a fan, said fan having variable speed control to transport said gas sample into said sample chamber at variable flow rates.

5. The TEC-SERS fiber optic probe of claim 1 wherein said optical emissions signal represents an analyte from said gas sample in contact with said SERS substrate, wherein said analyte is selected from the group that includes benzene, toluene, ethylbenzene, MTBE, TNT, RDX, cocaine, heroin, saran, xylene, mustard gas, and chlorinated solvents.

6. The TEC-SERS fiber optic probe of claim 1 further comprising a means for generating said optical excitation signal to irradiate said SERS substrate, operably coupled to said sample chamber.

7. The TEC-SERS fiber optic probe of claim 4 wherein said means for generating an optical excitation signal to irradiate said SERS substrate includes a laser.

8. The TEC-SERS fiber optic probe of claim 1 further comprising a means for detecting said SERS optical emissions signal, generated in response to said SERS substrate being irradiated by said optical excitation signal when an analyte is in contact with said SERS substrate.

9. The TEC-SERS fiber optic probe of claim 6 wherein said means for detecting a SERS optical emissions signal includes a spectrometer for detecting the spectral characteristics of said optical emissions signal.

10. The TEC-SERS fiber optic probe of claim 1 further comprising a heated membrane unit operably coupled to said inlet of said sample chamber.

* * * * *